US00PP30088P2

(12) United States Plant Patent
Dodd et al.

(10) Patent No.: US PP30,088 P2
(45) Date of Patent: Jan. 15, 2019

(54) APPLE TREE NAMED 'MAIA-T'

(50) Latin Name: ***Malus* x *domestica***
Varietal Denomination: MAIA-T

(71) Applicant: Midwest Apple Improvement Association, Newcomerstown, OH (US)

(72) Inventors: William Dodd, Newcomerstown, OH (US); David Doud, Wabash, IN (US); John Mitchel Lynd, Pataskala, OH (US); Gregory Miller, Carrollton, OH (US)

(73) Assignee: Midwest Apple Improvement Association, Newcomerstown, OH (US)

( * ) Notice: Subject to any disclaimer, the term of this patent is extended or adjusted under 35 U.S.C. 154(b) by 0 days.

(21) Appl. No.: 15/731,791

(22) Filed: Jul. 31, 2017

(51) Int. Cl.
*A01H 5/00* (2018.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Optima Law Group, APC

(57) ABSTRACT

A new and distinct variety of apple was identified from a population of seedlings derived from an open-pollinated 'Honeycrisp' block. The new variety, named 'MAIA-T,' is distinct from 'Honeycrisp' as 'MAIA-T' ripens mid-September, 2 weeks after 'Honeycrisp.' Unlike 'Honeycrisp,' 'MAIA-T' has purple skin, yellow ground color, and considerable russet. 'MAIA-T' fruit are medium sized, crisp, with more complex, sweet-tart flavors than 'Honeycrisp.' 'MAIA-T' does not maintain crisp texture in 35° F. storage for as long as 'Honeycrisp.'

3 Drawing Sheets

Latin name:
Latin name of the genus and species of the plant claimed: *Malus* x *domestica.*
Variety denomination:
Variety denomination: 'MAIA-T'.

BACKGROUND OF THE INVENTION

A new and distinct variety of apple was identified from a population of seedlings derived from an open-pollinated 'Honeycrisp' (U.S. Plant Pat. No. 7,197) block. This pollination was sanctioned as a part of the Midwest Apple Improvement Association apple breeding project. 'Honeycrisp' and other select varieties were cultivated with the intention of progeny testing open-pollinated seedlings. This superior seedling tree was identified from this progeny test at Pataskala, Ohio.

The seedling tree was planted as a 1-year-old tree at a commercial fruit orchard in Pataskala, Ohio in 2001 and grown among a population of several hundred siblings. Evaluations of fruit quality and tree growth parameters were begun in 2005 and this seedling was identified over several years as superior based upon tree growth habit, precocity, superior fruit quality, and harvest time. Utilizing grafting reproduction, the new apple tree variety was asexually propagated by Mitch Lynd in 2010 in Pataskala, Ohio and has been observed to remain true to the description set forth herein, through successive generations.

The new variety, named 'MAIA-T,' is distinct from 'Honeycrisp' as 'MAIA-T' ripens mid-September, 2 weeks after 'Honeycrisp' (FIG. 1). Unlike 'Honeycrisp,' 'MAIA-T' has purple skin, yellow ground color, and considerable russet (R.H.S. Color Chart Red-Purple 60A, Yellow-Orange 16B, and Yellow-Orange 22A, respectively). 'MAIA-T' fruit (FIGS. 2 & 3) are medium sized, crisp, with more complex, sweet-tart flavors than 'Honeycrisp.' 'MAIA-T' does not maintain crisp texture in 35° F. storage for as long as 'Honeycrisp' (FIG. 1).

BRIEF DESCRIPTION OF THE DRAWINGS

The accompanying photographs show typical specimens of the new variety depicted in color as true as is reasonably possible. 'MAIA-T' photographs were taken at Pataskala, Ohio.

FIG. 1. A chart showing that 'MAIA-T' is distinct from 'Honeycrisp' in harvest and storage windows.

DETAILED BOTANICAL DESCRIPTION

Figure 1:
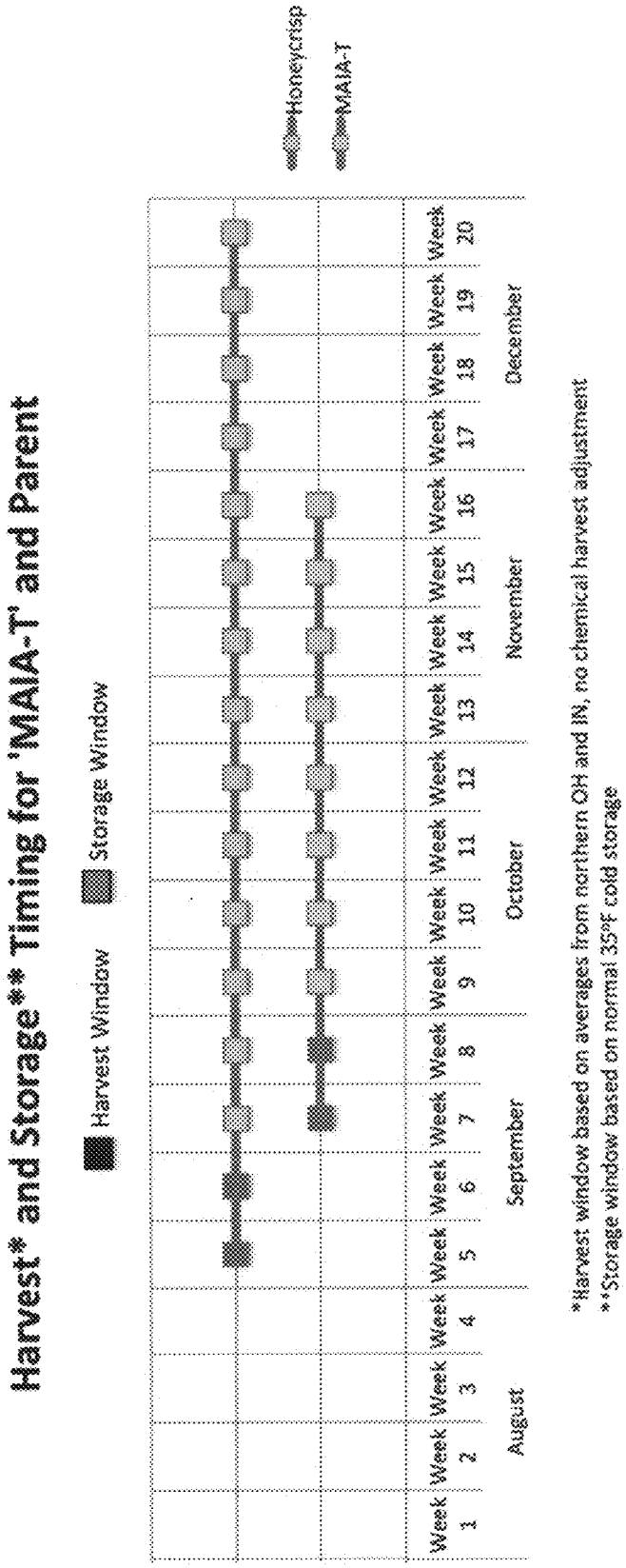
FIG. 1 was created from harvest data from Pataskala, Ohio, and storage data from Carrollton, Ohio.
Figure 2:
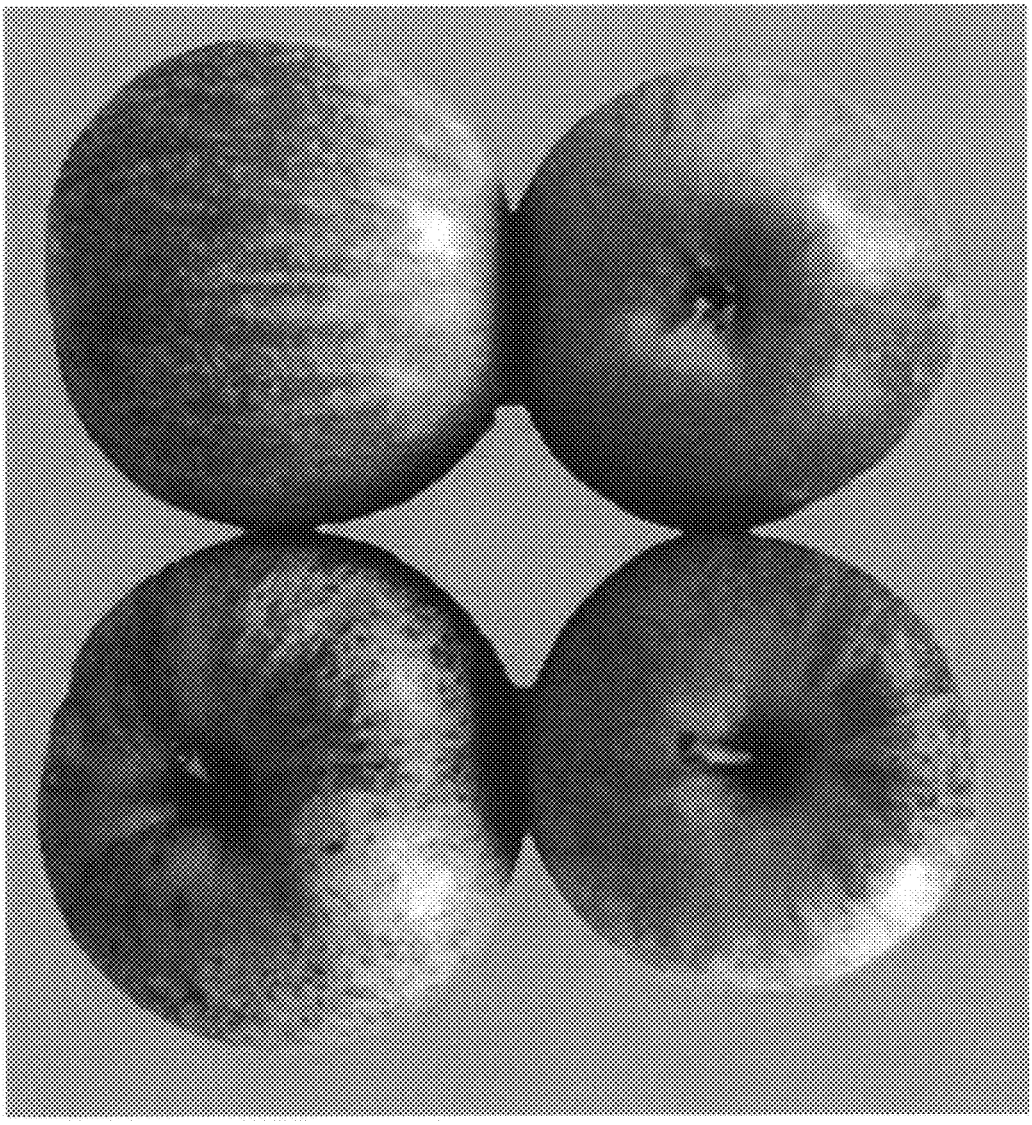
FIG. 2. An image of typical fruit of 'MAIA-T' at harvest time.
Figure 3:
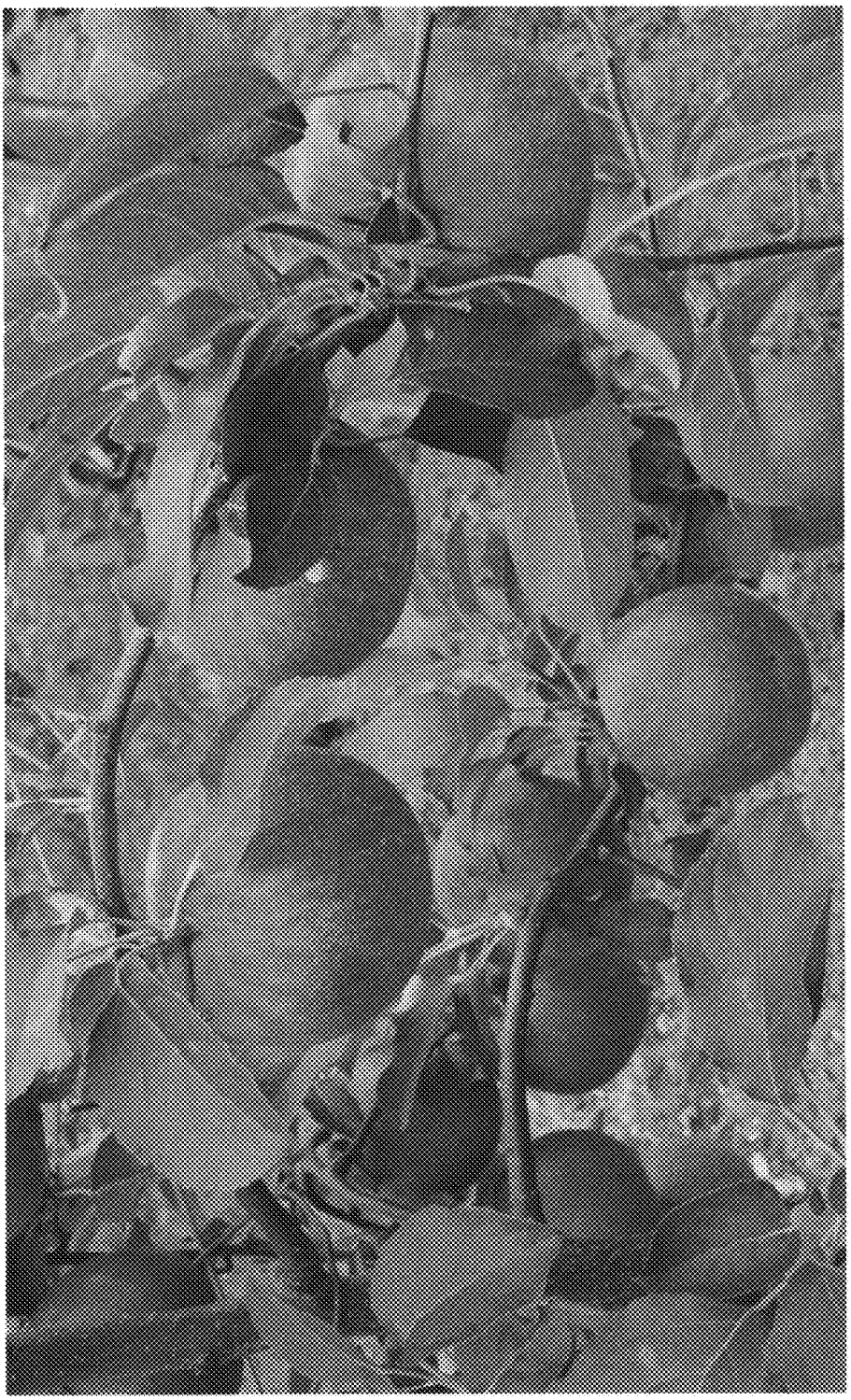
FIG. 3. An image of typical 'MAIA-T' trees bearing fruit in September in Ohio.

Color references are made to The Royal Horticultural Society Color Chart (R.H.S.) 2001 Edition.

Parentage: 'Honeycrisp' female parent and unknown male parent; open pollination conditions cultivated by Mitch Lynd at Pataskala, Ohio in 1999.

Grafted tree on B9 rootstock (reference tree):

*Age.*—12 years.
*Size.*—15' height, 8' spread.
*Vigor.*—Medium.
*Form.*—Round, spreading.
*Production.*—Very productive.
*Growth type.*—Spindle tree growth form, productive spurs located throughout tree.
*Bearing.*—Annual.

Trunk:

*Reference tree.*—3.5 cm at 15 cm height.

*Bark color.*—Greyed-Brown 199A.

*Lenticels.*—Oblong, 3×1 mm.

*Lenticel color.*—Greyed-Brown N199D.

*Lenticel density.*—2 lenticels/$cm^2$.

Branches:

3 *year old.*—8-9 mm in diameter, branch angle 80-90°; Greyed-Brown 199A.

2 *year old.*—5-6 mm in diameter, branch angle 60°; Greyed-Green 197A.

1 *year old.*—4-5 mm in diameter, branch angle 60-80°; Grey-Orange 166A.

Leaves:

*Size.*—Length 70-115 mm; width 45-65 mm.

*Texture.*—Leathery, crisp, wavy.

*Form.*—Ovate.

*Base.*—Roundly cuneate.

*Apex.*—Acute.

*Adaxial surface pubescence.*—None.

*Abaxial pubescence.*—Lightly pubescent.

*Adaxial surface color.*—Green Group N137B.

*Abaxial surface color.*—Green Group 143A.

*Veination.*—Pinnate, 7-9 major veins, mainly alternate; Yellow-Green 144B.

*Margin.*—Serrate.

*Petiole length.*—20-35 mm.

*Petiole width.*—2 mm.

*Petiole abaxial color.*—Yellow-Green 144B to Greyed-Purple 183A toward base.

*Petiole groove.*—Very shallow, depth 0.1 mm.

*Stipules.*—Present; 8-12 mm length; 1.5 mm width; Green Group 143A.

*Leaf glands.*—None observed.

Leaf buds:

*Length.*—4-5 mm.

*Width.*—4 mm.

*Color.*—Yellow-Green 149B with Greyed-Orange 166A overtones.

*Placement on branch.*—Alternate.

*Internode distance.*—20-30 mm.

Spurs: Present on 2 yr and older wood.

*Length.*—Varies from 8 to 150 mm.

*Relative proportion of spurs of each length.*—100-150 mm=2. 50-99 mm=2. 8-49 mm=7. Width: 4-7 mm.

Flowers at popcorn stage:

*Pedicel.*—Length 9-11 mm; width 2 mm.

*Pedicel color.*—Green Group 198A.

*Bud.*—Length 11-12 mm; width 8-11 mm.

Flowers at full bloom:

*Bloom time.*—Blooms slightly before 'Golden Delicious.' Bloom time varies with temperature, but is typically during the $4^{th}$ week of April in northeast Ohio.

*Bloom period.*—Approximately 7 days.

*Presentation.*—Showy.

*Fragrance.*—Aromatic.

*Fertility.*—Fertile.

*Number of flowers per cluster.*—5-6 with 5 typical.

Petals:

*Arrangement.*—Bases not overlapping; 5 petals per flower; each petal 20-24 mm length, 14-15 mm width.

*Color.*—Upper surface (inside) White Group NN155D; Lower surface (outside) slightly colored, Greyed-Green NN155C with Red-Purple 61A.

*Shape.*—Broadly ovate with occasional notching and ruffling.

*Veins.*—Distinct.

*Margins.*—Ruffled edges with notching ⅔ up the petal.

*Texture.*—Soft.

*Receptacle.*—Length 3-4 mm; width 3-3.5 mm; color Greyed-Purple 184B.

*Pedicel.*—Length 8-10 mm; width 2-2.5 mm; color Greyed-Green 197B.

*Sepals.*—5/flower; wedge-shaped, sharply pointed; length 5-6 mm; width 3-4 mm at widest point; adaxial and abaxial color Greyed-Green 197A.

*Stamens.*—16-18 in number.

*Anthers.*—Length 1.5-2 mm; width 1-1.5 mm; color Yellow Group 2D.

*Petal apex.*—Predominantly rounded with some fluting.

*Pollen.*—Present and abundant; color Yellow Group 10C.

*Filaments.*—Length 6-7 mm; width 0.5-1 mm; color Greyed-Green 157B.

*Pistil.*—Held above the anthers in majority of blossoms; color Yellow-Green 145B.

*Ovary.*—Length 2.5 mm; width 2.5 mm; color Green Group 143B.

*Style.*—Length 12-13 mm; styles are fused in bottom 4 mm only; width 0.5 mm; color Yellow-Green 144B.

*Stigma.*—Width 0.5-1 mm; held above the anther in the majority of blossoms; color Yellow-Green 151B.

Pollination requirements: Requires cross-pollination from diploid varieties with overlapping bloom; will pollinate diploid varieties of overlapping bloom.

Fruit:

*Maturity when described.*—3 month storage.

*Date of picking.*—Sep. 30, 2016.

*Size.*—Axial diameter 68-89 mm; Transverse diameter shortest point 35-50 mm; Transverse diameter longest point 59-70 mm.

*Fruit weight.*—162-240 g; Average 194 g.

*Form.*—Roundish, oblate, conic, side unequal.

*Cavity.*—Acute, deep, light russet in cavity.

*Basin.*—Shallow, relative to other variety, wide, smooth, regular.

*Calyx.*—Closed, tight.

Skin:

*Thickness.*—Medium.

*Tendency to crack.*—Little.

*Stripes.*—Heavy striping, russet.

*Lenticels.*—Irregular.

*Color.*—Red-Purple 60A.

*Ground color.*—Yellow-Orange 16B.

*Russet color.*—Yellow-Orange 22A.

Flesh:

*Aroma.*—Sweet, aromatic.

*Color.*—Yellow-White 158A.

*Texture.*—Crisp, firm, breaking, juicy.

*Eating quality.*—Excellent.

*Flavor.*—Sweet-tart, honeyed/scented.

Core: Small.

*Bundle area.*—1520 $mm^2$-2400 $mm^2$.

*Bundle.*—Conspicuous.

*Axial carpel length.*—6-10 mm.

*Locule.*—Closed.

*Seed cells.*—Walls thin, tough.

Seeds:

*Number perfect.*—6-11.

*Number in one cell.*—1-2.

*Length.*—7-9 mm.

*Breadth.*—4-5 mm.

*Color.*—Greyed-Orange 165A.

Stem:

*Length.*—13-26 mm.

*Average length.*—20 mm.

*Width.*—2-4 mm.

*Color.*—Greyed-Green 194B.

Use: Fresh market, dessert.

Shipping quality: Good.

Keeping quality: Moderate.

Drought tolerance: Average for domestic apple.

Tree winter hardiness: Average for domestic apple.

Disease:

*Resistance.*—Slight resistance to fireblight (Erwinia amylovora) and apple scab (Venturia inaequalis).

*Susceptibility.*—Susceptible to powdery mildew (Podosphaera leucotricha) and other fungal diseases.

Yield: Approximately 2.5 bushel/tree at 300 trees/acre yields 750 bushels/acre annually.

What is claimed is:

1. A new, distinct variety of apple tree named 'MAIA-T', as illustrated and described herein.

* * * * *